United States Patent [19]

Gorges

[11] 4,315,502
[45] Feb. 16, 1982

[54] LEARNING-RELAXATION DEVICE

[76] Inventor: Denis E. Gorges, 4392 State Rd., Cleveland, Ohio 44109

[21] Appl. No.: 84,051

[22] Filed: Oct. 11, 1979

[51] Int. Cl.³ .............................................. A61N 1/34
[52] U.S. Cl. .................................................. 128/1 C
[58] Field of Search .................... 128/24 A, 24.1, 732, 128/33, 1 R, 1 C, 630; 40/442, 455, 457; 35/22 R; 350/145, 45; 351/158, 48

[56] References Cited

U.S. PATENT DOCUMENTS

| 3,576,185 | 4/1971 | Schulz et al. | 128/1 C |
| 3,612,651 | 10/1971 | McCurdy | 40/457 |
| 3,712,292 | 1/1973 | Zentmeyer, Jr. | 128/1 C |
| 3,773,049 | 11/1973 | Rabicher et al. | 128/1 C |
| 3,826,250 | 7/1974 | Adams | 128/33 |
| 3,857,383 | 12/1974 | Sommerfeld et al. | 128/630 |

FOREIGN PATENT DOCUMENTS

| 2314014 | 10/1974 | Fed. Rep. of Germany | 128/1 C |
| 2846859 | 5/1979 | Fed. Rep. of Germany | 128/1 C |
| 1165541 | 10/1969 | United Kingdom | 128/1 C |
| 1422959 | 1/1976 | United Kingdom | 128/380 |
| 500802 | 4/1976 | U.S.S.R. | 128/1 C |

OTHER PUBLICATIONS

Beck, R. C., "ELF Magnetic Fields and EEG Entrainment," Apha-Metrics Company Publication 1978.

Primary Examiner—Robert W. Michell
Assistant Examiner—Francis J. Jaworski
Attorney, Agent, or Firm—Yount & Tarolli

[57] ABSTRACT

Disclosed is a device for relaxing, stimulating and/or driving brain wave form function in a human subject. The device comprises, in combination, an eye mask having independently controlled left and right eyepieces and a peripheral light array in each eyepiece, an audio headset having independently controlled left and right earpieces and a control panel which controls light and sound signals to the light arrays and earpieces, respectively. Various control functions allow simultaneous or alternating light and sound pulsations in the left and right light arrays and earpieces, as well as selective phasing between light and sound pulsations.

23 Claims, 8 Drawing Figures

LEARNING-RELAXATION DEVICE

BACKGROUND OF THE INVENTION

This invention relates to the art of learning and relaxation aids and more particularly to a device which releases psychological and physiological stress and tension primarily by stimulating the senses of hearing and sight.

Various devices have been developed in recent years for use in both stimulating and patterning brain functions in both the fields of psychology and learning. Thus, the so-called bio-feedback devices utilize electrical signals from various sensors placed on the body of a subject which sense such variables as skin temperature, pulse rate, blood pressure and the like. From a summation of these various data, the subject is provided with some form of feedback which is indicative of these various conditions. By concentrating on particular symptoms, an alteration in one or more of the variables may be induced which in turn alters the feedback. Commonly, an audio tone is utilized to indicate a particular mental or physical state and variations in the tone indicate differing mental or physical states. Eventually, the subject "learns" how to induce changes in his physical state without feedback. A typical bio-feedback device is described in U.S. Pat. No. 3,942,516.

Subliminal stimulation is also known to impart knowledge to a subject through subconscious mental functioning. A tachistoscopic visual image impressed upon the field of vision of a subject, such as on a motion picture or a television screen, can stimulate and be retained by a subject's subconsciousness even when the stimulus is of such short duration that the subject's conscious mind is totally unaware of its presence. Similarly, it is also known that audio subliminal stimulation is possible by overlaying an audio signal onto a normal pattern of audio input. U.S. Pat. Nos. 3,060,795 and 3,278,676 are illustrative of these concepts.

In the field of learning, sensory isolation, wherein distracting sensory inputs are suppressed, is well known. The common study carrel which limits peripheral vision and usually incorporates sound deadening panels is typical of such devices. Also known is a learning aid which incorporates a pair of eye goggles which act in a manner similar to blinders to limit a subject's peripheral vision, and, as described in U.S. Pat. No. 3,534,484, may also incorporate a source of an audio signal which acts to block out other distracting audio inputs. This combination affords the user a reduction in distracting sensory inputs and thereby assists in the development of concentration on a particular subject matter.

Modern theories of psychology and learning have identified various functional areas in the physical structure of the brain and central nervous system. Thus, the so-called left hemisphere of the brain is thought to be the source of logical reasoning and rote functioning of the human consciousness. Conversely, the so-called right brain hemisphere is thought to be the source of artistic, creative and imaginative functioning within the brain.

A similar division has been noted in front and rear brain functioning. The rear portion of the brain controlling the instinctual function of the body such as the central nervous system, the limbic system, etc. while human reasoning or social functioning is centered in the front portion of the brain.

Often the functioning of one hemisphere or portion is emphasized to the point of suppression of or conflict with the functioning of the other. Ideally, "whole" brain functioning would be utilized through a balancing of left and right, and front to back brain functions. In order to accomplish this, it is necessary to reduce the over-emphasized functioning and increase the under emphasized functioning to a point where there is cooperative functioning of both brain hemispheres, side to side and front to back.

It has been found that the brain utilizes wave patterns in order to function. It has also been found that light and sound stimuli can affect brain wave patterns and actually alter the flow of these brain wave patterns.

SUMMARY OF THE INVENTION

The present invention provides an apparatus for stimulating and coordinating whole brain wave function, which apparatus comprises in combination a source of pulsating light in an eye-covering mask which locates the light sources adjacent the left and right eyes of a subject and an audio headset which applies sound signals to the left and right ears of the subject.

In accordance with the invention, an eye mask generally in the form of goggles having left and right eyepieces includes a peripheral source of light for each eyepiece which may be independently controlled for pulsation frequency and light intensity. The mask incorporates a headband for securing the mask to the wearer's head and may also include integral air vents.

In a preferred embodiment of the invention, the eyepieces incorporate interchangeable lens and/or filter elements which may be colored lenses, prismatic lenses, mirrors and the like. Clear lenses may also be utilized.

In accordance with the preferred embodiment of the invention, the eye mask as above described, may further include a secondary pulsating light source located generally above and between the left and right eyepieces. A source of extremely low frequency (1-30 Hz) electromagnetic force fields may also be provided adjacent each eyepiece and electrically connected to pulse at the frequency and intensity of its associated light source and/or audio source.

The eye mask as above described is used in conjunction with an audio headset which is similar to a set of stereo headphones. Audio signals to left and right eyepieces are controlled independently along with light pulsations in the eye mask.

The eye mask and headset are connected, preferably through a single umbilical connector, to a control panel. The control panel incorporates controls for the intensity of both the light source and the sound volume. A pulsation frequency control is also utilized.

In the preferred embodiment, the control panel as above described may further include switching means which permits simultaneous left and right pulsations of both the light sources and sound outputs or may also permit alternating left and right pulsations in each mode. A second switching means may also be provided which alternates a light pulse with a sound pulse in one position and synchronizes light and sound pulses in a second position. Thus, in combination, the two switching means permit four possible combinations of alternating and synchronous pulsations between the left and right light and sound sources. Each of these switching modes stimulates a particular area of the brain to effect an alteration in brain wave form functioning.

Further in accordance with the invention, a heartbeat sound output is provided by the control panel for overlaying a pulsating heartbeat sound on various other audio signals. A heart rate control is also provided for increasing or decreasing the heartbeat sound rate.

In accordance with yet another embodiment of the invention, provision is made for input of audio signals from external sources, such as tape, phonograph, voice microphone or the like. The external audio inputs may also be independently controlled for volume.

BRIEF DESCRIPTION OF THE DRAWINGS

The invention is illustrated in the accompanying drawings showing a preferred embodiment including specific parts and arrangements of parts. It is intended that the drawings included as a part of this specification be illustrative of a preferred embodiment of the invention only and should in no way be considered as a limitation upon the invention itself.

DETAILED DESCRIPTION OF PREFERRED EMBODIMENTS AND THE DRAWINGS

Figure 1:
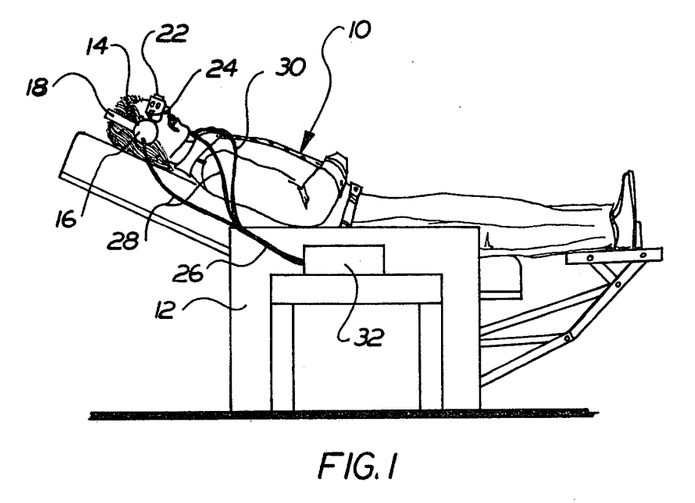
FIG. 1 is a side elevational view illustrating one environment in which the invention may typically be employed.

Referring now to the drawings which are for the purposes of illustrating a preferred embodiment of the invention only and should not be construed as a limitation upon same, FIG. 1 illustrates the learning, relaxation and stress reduction device in accordance with a preferred embodiment of the invention worn for use by a human subject 10. In order to achieve maximum effect from the device, the human subject 10 is preferably supported in a comfortable reclining or semi-reclining position on a table or, as shown in FIG. 1, on a comfortable reclining chair 12. The form of body support is unimportant to the invention but the subject 10 should preferably be in a comfortable position whether seated or fully reclined. Other reclining supports such as padded tables, water mattresses, air mattresses or the like are possible. Variable frequency vibrators or massagers may also be incorporated into the body support to effect greater subject relaxation and entrainment of brain wave forms.

The learning-relaxation device generally comprises an audio headset 14 having a pair of earpieces 16 connected by an adjustable headband 18. An eye mask 20 having eyepieces 22 is worn covering the eyes of the subject 10 and is held in place by an elastic headband 24. A signal input umbilical cord 26 which divides to form headset umbilical cord 28 and eye mask umbilical cord 30 is connected to a signal output and control panel 32 supported within easy reach of the subject 10.

The control panel 32 contains various controls for light and sound signals which are provided to the headset 14 and the eye mask 20. As shown in FIG. 1, umbilical 26 has a divided Y-form to connect to the headset 14 through headset umbilical 28 and to the eye mask 20 through eye mask umbilical 30. This is merely one preferred form of umbilical connection and other forms of connection are possible and contemplated within the scope of the present invention. For example, the eye mask umbilical 30 may be connected to an appropriate portion of the headset 14 and the umbilical 26 could connect directly with the headset 14 carrying both signals for the headset 14 and the eye mask 20.

Figure 2:
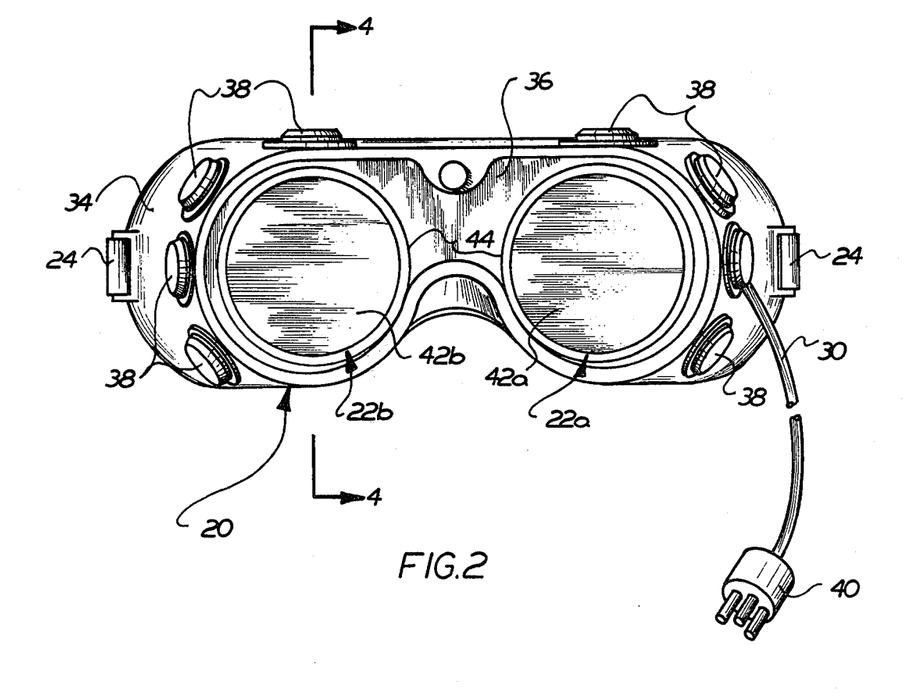
FIG. 2 is a front elevational view of an eye mask used in accordance with a preferred embodiment the invention.

As illustrated in FIG. 2, the eye mask 20 comprises a resilient, head-conforming body portion 34 and a generally rigid front panel 36 upon which the left and right eyepieces 22a and 22b, respectively, are mounted. The elastic headband 24 serves to secure the eye mask 20 over the subject's eye.

The preferred form of the eye mask 20 preferably incorporates a number of vents 38 located on the body 34 so as to permit air circulation within the eye mask 20. Eye mask control umbilical 30 extends outwardly from the body 34 of eye mask 20 and, as shown in FIG. 2, has a connector plug 40 located at the remote end thereof. The connector plug 40 may be connected to an appropriate socket located either on the headset 14 or on the control panel 32 as desired, or, as illustrated in FIG. 1, the umbilical 30 may be spliced directly into control umbilical 26 and therefore no plug is necessary.

The eyepieces 22a, 22b each incorporate at least one lens element 42a, 42b which is retained in place on the front panel 36 by a pair of retainer rings 44. As more fully described hereinafter, the lens elements 42a, 42b may be clear glass, transparent or translucent color filters, prismatic lenses, mirrors, opaque lenses and the like or any combination of these forms. Also, it is possible to utilize the eye mask 20 without any lens elements 42a, 42b mounted so that there is merely an opening through the eyepieces 22a, 22b.

Figure 3:
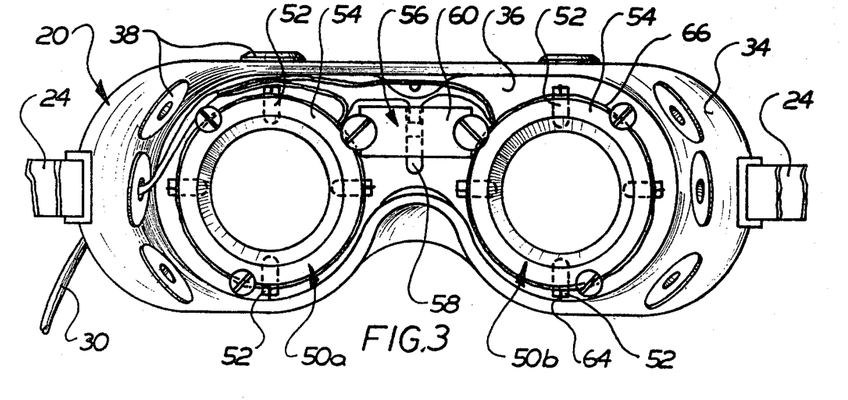
FIG. 3 is a rear elevational view of the eye mask shown in FIG. 2.
Figure 4:
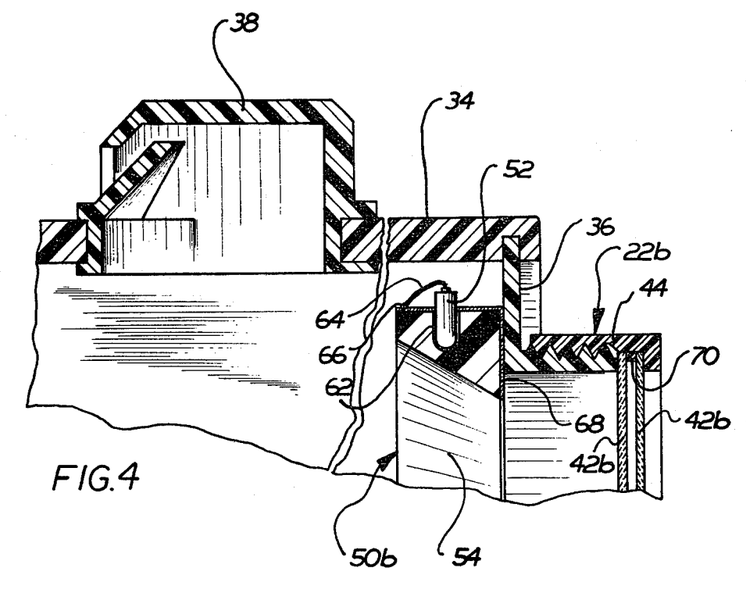
FIG. 4 is an enlarged cross sectional view of a portion of the eye mask shown in FIG. 2 taken along line 4—4 thereof.

As illustrated in FIGS. 3 and 4, a circumferential peripheral light array 50a, 50b is mounted behind each eyepiece 22a, 22b respectively, on the back or inside of front panel 36 within the body 34 of the eye mask 20. In the preferred embodiment, the light arrays 50a, 50b include a series of miniature lamps 52 disposed radially around an annular diffuser ring 54. The diffuser ring 54 acts to conduct light from the miniature lamps 52 around its periphery so that a ring of light is produced around the periphery of each eyepiece 22a, 22b. It will be understood that other forms of light arrays 50a, 50b may be provided such as an annular fluorescent tube or the like, the only requirement being that the intensity of the light be variable and that instantaneous flashing of the light source be possible.

In the preferred embodiment of the invention, a central light source 56 is provided. The central light source 56 which includes a miniature lamp 58 and diffuser 60 is provided to stimulate the wearer's pituitary and pineal glands which are located in the front of the brain above and between the eyes. It has been found that these glands contain tissue which responds to light input and the placement of a central light source 56 offers additional learning and relaxation advantages due to smooth flow of brain wave activity back and forth, left to right when included along with the peripheral light arrays 50a, 50b.

Control umbilical 30 enters the interior of the body 34 of the mask 20 through one of the vents 38 as shown in FIG. 3. Appropriate wires for the control of electrical input to each light array are attached to each light array 50a, 50b and to the central light source 56. In the operation of the learning device in accordance with the invention, the light arrays 50a, 50b may be adjusted for light intensity and may be flashed either simultaneously or alternately with a varying flash or pulsation rate.

As clearly seen in FIG. 4, peripheral light array 50b comprises a solid annular ring 54 which is constructed of a light-diffusing substance such as plexiglass or other transparent or translucent material. Openings 62 are provided radially around the periphery of the annular ring 54 to receive miniature lamps 52 therewithin. The lamps 52 may be connected as by a conductor wire 64 in series to a peripheral electrical conductor 66 which circumscribes the periphery of the light array 50b. To assist in the light diffusion function of the annular ring 54, a coating 68 may be provided on appropriate surfaces of the ring 54 to assist in reflection and diffusion of the light emanating from the miniature lamps 52. The coating may be of any type such as a white enamel, metal foil or any similar material which assists in the light diffusion function.

Also shown in FIG. 4, the lens elements 42b are retained in the eyepiece 22b by the threaded retaining ring 44. A plurality of lens elements 42a, 42b may be provided in each of the eyepieces 22a, 22b to enhance various visual effects of the light arrays 50a, 50b. Thus, the lens elements 42b may include a clear lens, various colored lenses, reflectors, prismatic lenses, opaque lenses, or any similar form of lens element. When a plurality of such lens elements 42b are mounted, a resilient gasket 70 is preferably imposed therebetween to avoid possible breakage of the lens element should the retaining ring 44 be turned to an extremely tight position.

Figure 5:
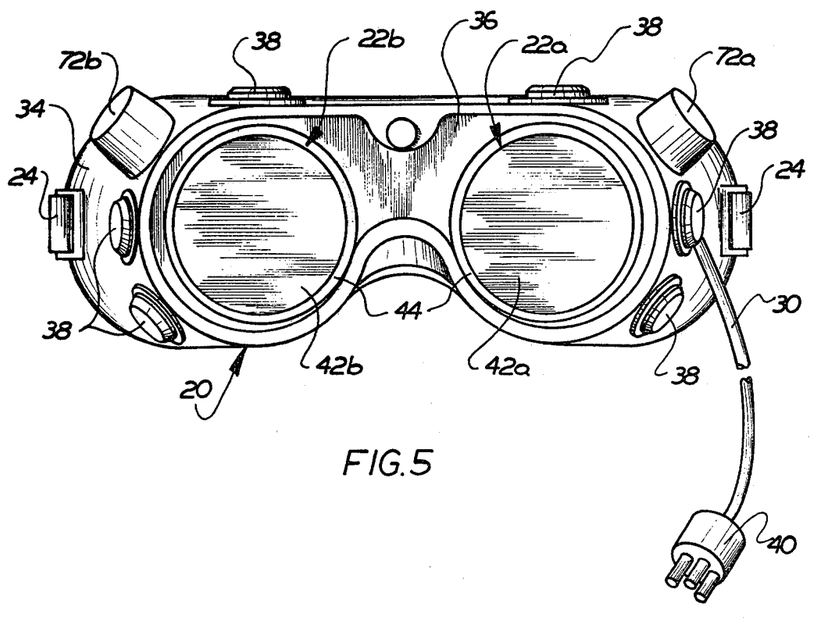
FIG. 5 is a side elevational view in partial section of the eye mask shown in FIG. 2 illustrating an alternative embodiment of the invention which includes an extremely low frequency electromagnetic oscillating coil.

It has been found that extremely low frequency (ELF) oscillating electromagnetic fields have a stimulating and driving effect on the electrical activity of the brain hemispheres of a human subject. It is therefore contemplated within the scope of this invention that a source of ELF electromagnetic energy be provided. As shown in FIG. 5, the eye mask 20 may include a pair of left and right ELF electromagnetic oscillating coils 72a, 72b which are of a type known in the art and are located adjacent the respective eyepieces 22a, 22b on the body 34 of the eye mask 20.

The ELF electromagnetic oscillating coils 72a, 72b are positioned on the eye mask 20 so that when the eye mask is worn by the user, the ELF electromagnetic coils 72a, 72b are adjacent the temple areas of the subject. The coils may conveniently be mounted in place of one of the vents 38 in the body 34 of eye mask 20.

The electromagnetic coils 72a, 72b are appropriately connected with a conductor wire to the associated left and right arrays 50a, 50b so that each coil 72a, 72b is activated simultaneously with its associated light array 50a, 50b.

An alternative to the placement of electromagnetic oscillating coils 72a, 72b on the eye mask 20 would be the placement of a pair of ELF electromagnetic radiators, such as Schuman coils, in the room in close proximity to the subject and connected to the control panels 32 for an alternating and pulsating output.

Figure 6:
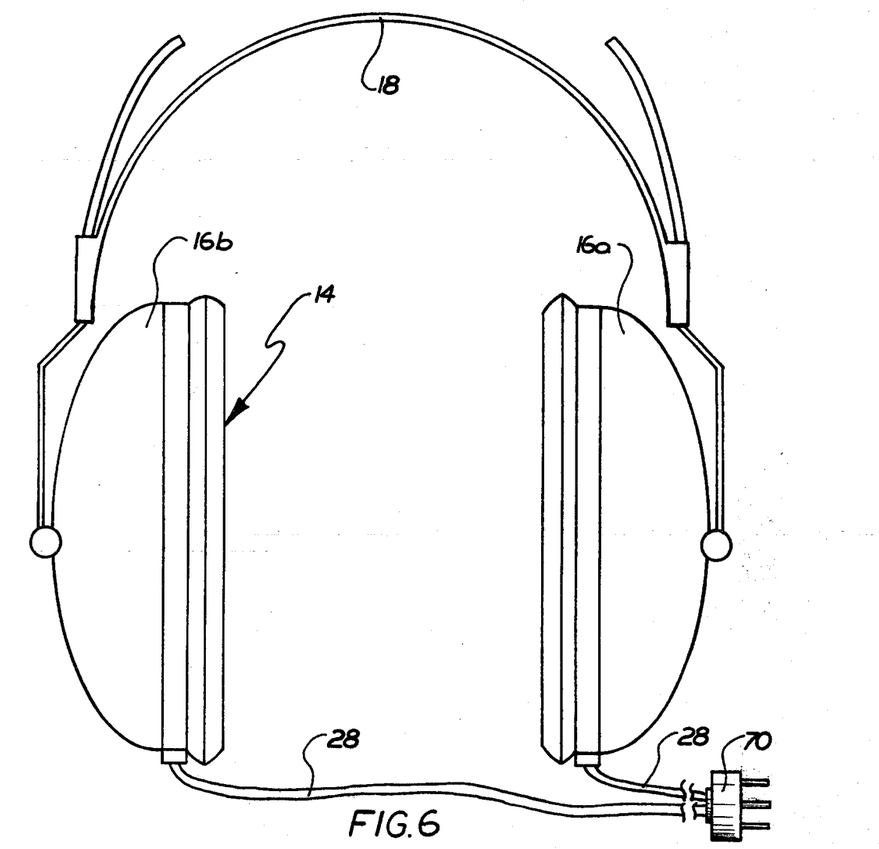
FIG. 6 is a front elevational view of a preferred form of headset utilized in accordance with the invention.

FIG. 6 shows a preferred form of headset 14 having a pair of earpieces 16a, 16b connected by a headband 18. The form of the headset 14 is unimportant to the present invention and the headset 14 may take the physical form of any common set of stereo headphones or ear plugs. The only requirement of the headset is that the speakers which are located within the earpieces 16a, 16b must be independently controllable for on and off function in a manner similar to normal stereo headphones. Input umbilical 28 is provided to supply signals to each of the earpieces 16a, 16b and an appropriate connector 74 may be provided to connect the headset 14 for signal input from the signal source, such as control panel 32. Although not shown in the Figures, a receptacle may be provided on one of the earpieces 16a, 16b for attaching the light control umbilical 30 from the eye mask 20. In this manner, the plurality of umbilical cords may be avoided resulting in a neater appearance for the device.

Figure 7:
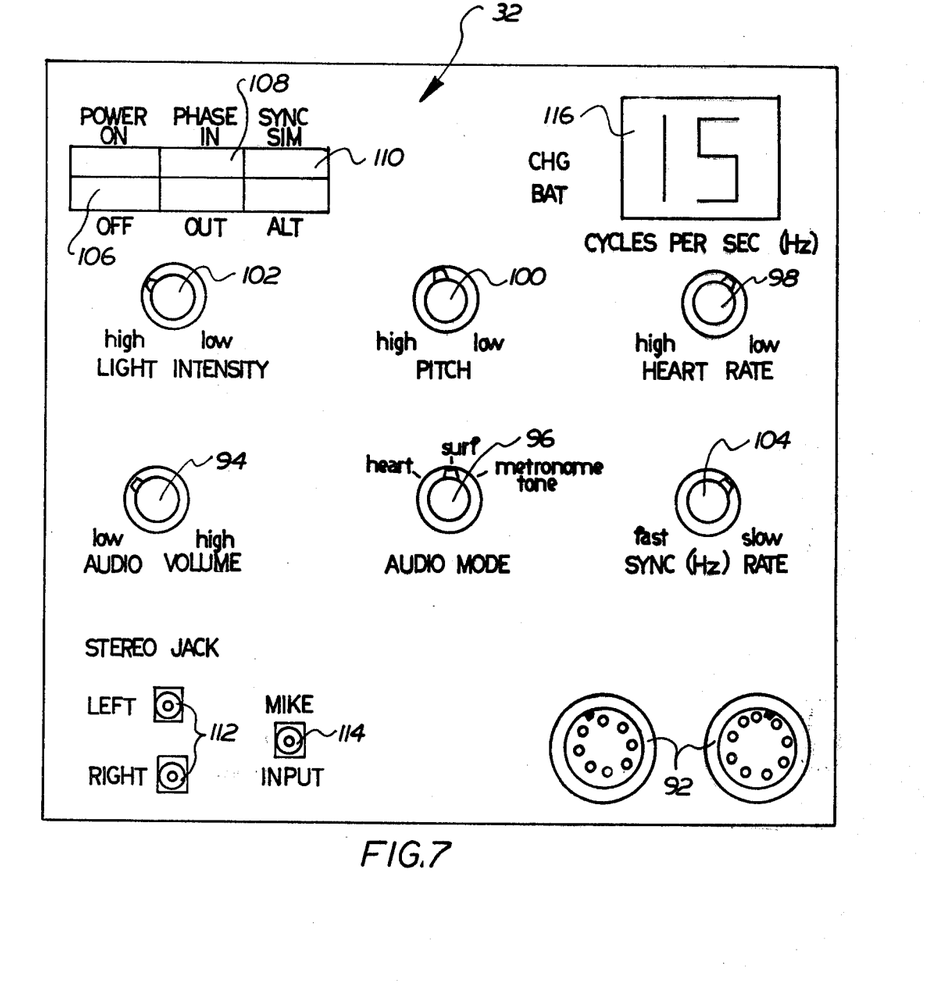
FIG. 7 is a plan view of one form of control panel utilized in a preferred embodiment of the present invention.

FIG. 7 illustrates one form of control panel 32 which may be utilized in accordance with the invention to control the operation of headset 14 and eye mask 20. At least one umbilical receptacle 92 is provided for connecting light and sound control umbilical 26 to the control panel 32. In the preferred embodiment, at least two receptacles 92 are provided for attaching at least two control umbilicals 26 to operate two learning-relaxation devices simultaneously.

The control functions include a variable volume control 94 for controlling the volume of the audio signal provided to the headset 14. An audio mode control 96 is provided for selecting various audio output signals to the headset 14. A heartbeat sound, a tocking metronome sound, a variable pitch tone and a surf or "white noise" sound are among the preferred audio modes which are selectable by the mode control 96.

In the preferred embodiment, a heartbeat sound is constantly provided and when other audio modes are selected, the heartbeat sound is overlayed onto the other selected sound. A variable heart rate control 98 is provided which varies the rate of pulsation from about 20 to about 220 heartbeats per minute.

When a tone audio output mode is selected, variable pitch control 100 may be used to selectively alter the pitch of the tone from a very low frequency (about 70 Hz) to a high frequency (about 7 kHz).

A variable light intensity control 102 is provided for selectively varying the intensity of the light signal transmitted to the light arrays 50a, 50b, 56 of the eye mask 20.

A variable pulse rate control 104 selectively varies the flashing and sound pulse rate in the signal output to the headset 14 and the eye mask 20.

In the operation of the learning-relaxation device in accordance with the invention, the headset 14 and eye mask 20 are connected through their respective umbilicals to the control panel and umbilical receptacle 92. An on-off rocker switch 106 is moved to the "ON" position. At that point, the light arrays 50a, 50b, 56 will produce a pulsating light at an intensity which corresponds to the light intensity control 102 and at a pulsation rate according to the selected rate on pulse rate control 104. In a similar manner, a pulsating sound will be emitted by the headset 14 at a volume which is selected by volume control 94. The character of the sound will be that as selected by the audio mode selector 96 and the heartbeat sound will be at a rate which corresponds to that selected by heart rate control 98.

A phase selector 108 is provided for selectively phasing the pulsating light and sound between the eye mask 20 and the headset 14. Thus, the phase selector may be positioned so that the light and audio signals are "IN" phase, that is that a sound is produced in one or both ears at the same time that the light arrays are pulsating on. Conversely, when the phase selector is moved to the "OUT" position, the light and sound pulses are out of phase, that is the lights are on when the sound is off and vice versa.

A synchronizing control 110 is also provided which comprises a rocker switch which is selectable for simultaneous or alternate synchronization of the light and sound pulses. Thus, when synchronous control 110 is in the simultaneous position, both light arrays 50a, 50b pulsate simultaneously. Similarly, sound input into both earpieces 16a, 16b is simultaneous. Conversely, when synchronization selector is in the alternating position, the signals are divided to both the light arrays 50a and 50b and the earpieces 16a and 16b so that left side light array 50a and the left side earpiece 16a pulse simultaneously and alternate with simultaneous pulsation of right light array 50b and right earpiece 16b.

Thus, by selectively positioning the phase and synchronizing controls 108, 110, four combinations of pulsating light and sound and left and right inputs are possible. The four switching combinations stimulate for separate areas of brain wave functioning.

Brain wave functioning and stimulation of various areas of the brain can be effected by the four combinations of phasing and synchronizing through controls 108 and 110 respectively. When left and right inputs are synchronized for simultaneous pulsation and the light and sound pulses are in phase, all areas of the brain are simultaneously stimulated. When the light and sound inputs are in phase but alternate from left to right in both modes, there is a cross communication of brain wave functioning between the left and right hemispheres resulting in lateral awareness and cooperation and communication between the hemispheres. When the light and sound inputs are out of phase and left and right light inputs and left and right sound inputs are synchronized, there is alternating front and back stimulation for both brain hemispheres. The light inputs stimulate the rear brain while the sound input affects the front portion of the brain. In the final switching mode, the light and sound inputs are out of phase and each alternate from left to right, thus, cross stimulating both the left and right hemispheres and the front and back cortical areas of the brain. This results in total external awareness and constant scanning of the various brain functional areas.

With the other controls, the light intensity may be raised or lowered, the audio volume may be similarly raised or lowered, the pulse rate may raised or lowered and the overlying heartbeat rate may be raised or lowered. If the audio mode selector 96 is selected for tone input, the pitch of the tone is also selectively variable. These combinations of controls offer the user a broad range of control functions for the light arrays 50a, 50b and the sound emanating from the earpieces 16a, 16b to affect various states of awareness and brain wave function.

Provision is also made for input from additional external sources of audio input which may be selected independently or impressed upon any of the other audio modes selected by mode selector 96. Thus, a pair of left and right stereo input jacks 112 are provided for connecting the output of various preprogrammed audio devices such as a radio, tape deck, record changer and the like. Further, a microphone input jack 114 is provided so that communication with the user or between simultaneous users is possible.

A digital display 116 may optionally be provided in accordance with a preferred embodiment of this invention. The digital display may be connected to give a digital read out of one or more control panel functions such as heart rate or pulsation rate.

Figure 8:
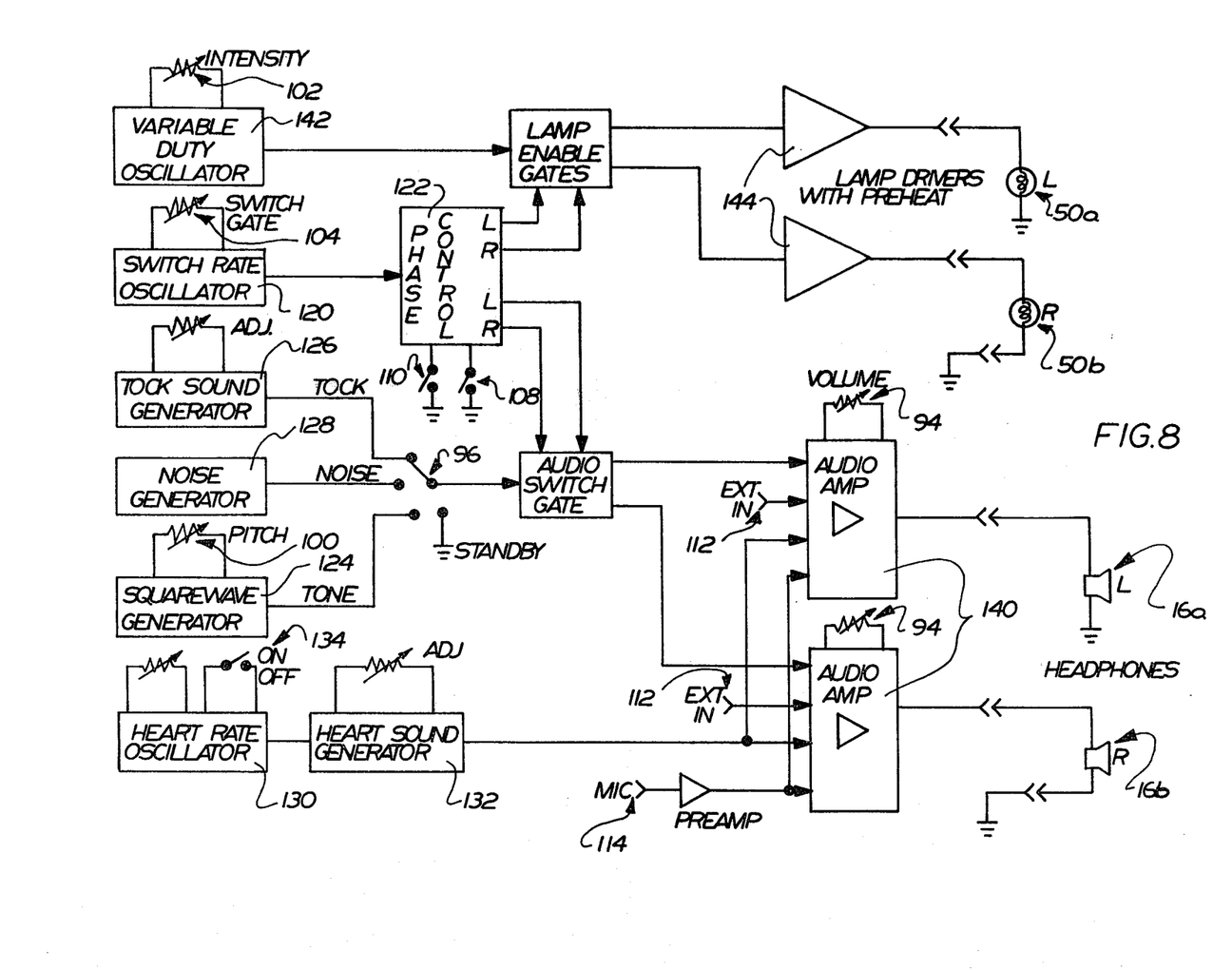
FIG. 8 is a block diagram of the circuitry of the control panel shown in FIG. 7.

As shown in the block circuit diagram of FIG. 8, a switch rate oscillator 120 incorporates variable switch rate control 104. An astable oscillator serves as a clock source which is divided to generate a perfectly symmetrical squarewave, thus insuring exactly equal on-off commands at a rate ranging from 1 to 30 Hz. A phase control 122 controls the synchronization and phasing of the switch rate oscillator output through phase switch 108 and synchronization switch 110 as previously described.

Several sound generators are provided. A squarewave generator 124 produces a perfectly symmetrical squarewave tone which may be varied by pitch control 100 through a range of about 70 Hz to 7 KHz.

A tock sound generator 126 is provided to give a familiar metronome-type "tic-toc" sound which is synchronized with the switch rate oscillator 120.

A noise generator 128 produces a surf sound or white noise which is generated by an emitter-base junction of a transistor.

A standby position for audio mode control 96 is provided so that none of the sound generators 124, 126, 128 are effective.

A variable heart rate sound is provided by heart rate oscillator 130 in conjunction with heart sound generator 132. The heart rate is varied by heart rate control 98 for a rate of 20 to 220 beats per minute. An internal ON/OFF switch 134 may also be provided. The variable heartbeat sound occurs when pulses are emitted from the heart rate oscillator. The pulses excite a twin-T oscillator within heart sound generator 132 to produce a damped sinusoid. A diode provides a slight accentuation of every other beat, simulating the snap of heart muscles. The heartbeat sound generator is not connected to audio mode control 96 and therefore a heartbeat sound is overlayed on all switch positions for audio mode control 96.

External inputs, such as mike input 114 and stereo inputs 112 are similarly unswitched and feed directly into audio amplifiers 140. All audio inputs including the various sound generators and heartbeat generators as well as the mike and stereo inputs are amplified in audio amplifiers 140 and audio signals are transmitted to the speakers located within the earpieces 16a, 16b of the headphones 14. Alternatively, inputs from external sources may be independently controlled for volume by separate amplifiers.

A variable duty oscillator 142 is used to control the brightness of the light arrays 50a, 50b and incorporates variable light intensity control 102. Lamp drivers 144 receive the light signal inputs from switch rate oscillator 120 and variable duty oscillator 142 to produce pulsating light flashes in the light arrays 50a, 50b. Preheat resistors are provided in the lamp drivers 144 to preheat the lamp filaments thereby improving lamp brightness response time. Further, the incandescent in-rush current is greatly reduced, thereby improving lamp driver reliability. When a central light source 56 is provided, it is preferably connected to only one of the light arrays 50a, 50b for pulsation with that light array. Similarly, when the ELF electromagnetic oscillating coils 72a, 72b are provided, they are connected for pulsation either with their respective associated left or right light array 50a, 50b or left or right earpiece 16a, 16b.

The control panel 32 may be powered by any of various power sources such an internal batteries, an external battery pack, or other source of DC power such as an AC rectifier-transformer or other similar device.

From the foregoing, it can be seen that the present invention provides an apparatus for stimulating brain function, which apparatus comprises in combination pulsating light arrays 50a, 50b in an eye covering mask 20 which locates the light arrays 50a, 50b adjacent the left and right eyes and an audio headset 14 which applies sound signals to the left and right ears of the wearer.

In accordance with the invention, an eye mask 14 generally in the form of goggles having left and right eyepieces 22a, 22b includes a light array 50a, 50b for each eyepiece 22a, 22b which may be independently controlled for pulsation frequency and light intensity. The eye mask 20 incorporates a headband 24 for securing the mask to the wearer's head and may also include integral air vents 38.

In a preferred embodiment of the invention, the eyepieces 22a, 22b incorporate interchangeable lenses or filter elements 42a, 42b which may be colored lenses, prismatic lenses, mirrors and the like.

In a preferred embodiment of the invention, the eye mask 20 may further include a secondary pulsating light source 56 located generally above and between the left and right eyepieces 22a, 22b. A source of extremely low frequency electromagnetic force fields such as extremely low frequency electromagnetic oscillating coils 72a, 72b may also be provided adjacent each eyepiece 22a, 22b and electrically connected to pulse at a frequency and intensity of its associated light array 50a, 50b or earpiece 16a, 16b.

The eye mask 20 and the headset 14 are connected through an umbilical connector wire 26 to a control panel 32. The control panel 32 incorporates controls 102, 94 for the intensity of both the light source and the sound volume, respectively. A pulsation frequency control 104 is also provided.

The control panel 32 may further include a two-position synchronizing switch, which in a first position permits simultaneous left and right pulsations of light from both the light arrays 50a, 50b and the sound from earpieces 16a, 16b and, which in a second position permit alternating left and right pulsations in each of the light and sound devices. A second phase switch 108 may also be provided which alternates the light pulse with the sound pulse in a first position and synchronizes the light and sound pulses in a second position. Thus, in combination, the two switching means 108, 110 permit four possible combinations of alternating and synchronous pulsations between the left and right light and sound sources to affect brain wave functioning from areas of the brain.

A heartbeat sound signal is also provided by the control panel 32 for overlaying a heartbeat sound on the various other audio signals. A heart rate control 98 is provided for increasing or decreasing the heartbeat sound rate.

Provision is also made for the input of audio signals from an external source by the provision of stereo jacks 112 and a microphone input 114.

In the operation of the above device, the subject places the eye mask 20 and the headphones 14 in position on his head and with the control panel 32 switched to the "ON" position by switch 106. The subject is able to control the intensity and pulse rate of the light and sound sources through the various control functions to produce stimulii which act to relax and/or stimulate brain functioning through the senses of hearing and sight.

While the invention has been described in the more limited aspects of a preferred embodiment thereof, other embodiments of the invention have been suggested and still others will occur to those skilled in the art upon a reading and understanding of the foregoing specification. It is intended that all such embodiments be included within the scope of the invention as limited only by the appended claims.

Having thus described my invention, I claim:

1. A learning-relaxation device for stimulating the central nervous system and the brain waves of a human subject having left and right eyes and left and right ears comprising:

light means providing pulsating light signals individually to the left and right eyes of the subject and for limiting at least peripheral vision in the left and right eyes, sound means operable independently of said light means and providing at least one pulsating sound signal individually to the left and right ears of the subject while blocking ambient sound to both left and right ears, and control means for individually varying frequency and intensity of each of said pulsating signals and phase of one of said signals relative to the other of said signals.

2. The device as set forth in claim 1 wherein said light means comprises an eye mask having means for securing said eye mask on the subject in a position covering the left and right eyes and having left and right eyepieces located respectively adjacent the left and right eyes and further including left and right peripheral light arrays located respectively around at least a portion of the periphery of said left and right eyepieces.

3. The device as set forth in claim 2 wherein said control means includes means for permitting simultaneous pulsating of said left and right light arrays.

4. The device as set forth in claim 3 wherein said sound means comprises left and right earpieces and said control means includes means for permitting simultaneous pulsating of said left and right earpieces with said left and right light arrays.

5. The device as set forth in claim 3 wherein said sound means comprises left and right earpieces and said control means includes means for permitting simultaneous pulsating of said left and right earpieces out of phase with said left and right light arrays.

6. The device as set forth in claim 2 wherein said control means includes means for permitting alternating pulsating between said left and right light arrays.

7. The device as set forth in claim 6 wherein said sound means includes left and right earpieces and said control means includes means for permitting alternating pulsating between said left and right earpieces in phase with said left and right light arrays.

8. The device as set forth in claim 6 wherein said sound means includes left and right earpieces and said control means includes means for permitting alternating pulsation between said left and right earpieces out of phase with said left and right light arrays.

9. A device, as set forth in claim 1, further comprising said control means including
switching means for selectively synchronizing and alternating the light and sound signals to said light arrays and earpieces in and out of phase with each other.

10. A learning and relaxation device for stimulating the central nervous system and the brain waves of a human subject having left and right eyes and left and right ears comprising:
an eye covering eye mask having left and right eyepieces;
each eyepiece including a peripheral light array which is electrically connected for individual control of light intensity and off-on switching;
an audio headset having left and right earpieces which independently supply sound signals to the left and right ears, and
a control panel connected to both said eye mask and said headset, said control panel including a plurality of sources of sound signals, means for selecting at least one of said sound signals, a variable volume control for said sound signals, a generator of light signals, means for varying the intensity of said light signals, pulsation means for pulsating said light and sound signals, switching means for selectively synchronizing and alternating the light and sound signals to said light arrays and earpieces in and out of phase with each other.

11. The device as set forth in claim 10 wherein said control panel further includes a heartbeat sound generator and means for selectively varying the heart rate of said heartbeat sound generator.

12. The device, as set forth in claim 10, wherein said control panel includes means for supplying a plurality of overlying sound signals simultaneously to said sound means.

13. The device, as set forth in claim 12, wherein said means for supplying a plurality of overlying sound signals includes a heartbeat sound generator.

14. The device, as set forth in claim 13, wherein said heartbeat sound generator has a variable rate control.

15. The device, as set forth in claim 12, wherein said means for supplying a plurality of overlying sound signals includes a microphone and microphone input means.

16. The device, as set forth in claim 12, wherein said means for supplying a plurality of overlying sound signals includes programmed sound means and input for said programmed sound means.

17. The device, as set forth in claim 12, wherein said control panel includes a variable volume control for said means for supplying a plurality of overlying sound signals.

18. The device, as set forth in claim 12, wherein said control panel includes a tone signal generator.

19. The device, as set forth in claim 18, wherein said tone signal generator includes a variable pitch control.

20. The device, as set forth in claim 10, further including a central light source located on said eye mask in a position generally between said left and right eyepieces.

21. The device, as set forth in claim 10, further including left and right extremely low frequency electromagnetic field oscillating coils located on said eye mask adjacent said left and right eyepieces.

22. The device, as set forth in claim 21, wherein said left electromagnetic coil and left light array are electrically connected for simultaneous pulsation and said right electromagnet and said right light array are electrically connected for simultaneous pulsation.

23. A learning-relaxation device for stimulating the central nervous system and the brain waves of a human subject having left and right eyes and left and right ears comprising:
light means for providing pulsating light signals independently to the left and right eyes of the subject and for limiting at least peripheral vision in the left and right eyes,
sound means for providing at least one pulsating sound signal independently to the left and right ears of the subject while blocking ambient sound to both left and right ears, and
control means for individually controlling frequency and intensity for each of said pulsating light and sound signals,
said control means including selective means for selectively stimulating through the eyes and ears all,
by light and sound inputs in phase but alternating from left to right by cross stimulation,
by light and sound inputs out of phase but with left and right light inputs and left and right sound inputs synchronized by alternate stimulation, or
by light and sound inputs out of phase and each alternating from left to right by cross and alternate stimulations
light and sound stimulated areas of the brain.

* * * * *